(12) United States Patent
Clarida et al.

(10) Patent No.: US 11,980,420 B2
(45) Date of Patent: May 14, 2024

(54) DYNAMIC ADJUSTMENT OF FLASH INTENSITY BASED ON RETINAL PIGMENTATION

(71) Applicant: Digital Diagnostics Inc., Coralville, IA (US)

(72) Inventors: Warren James Clarida, Iowa City, IA (US); Ryan Earl Rohret Amelon, University Heights, IA (US); Abhay Shah, Burlington, IA (US); Jacob Patrick Suther, Burlington, IA (US); Meindert Niemeijer, Coralville, IA (US); Michael David Abramoff, University Heights, IA (US)

(73) Assignee: Digital Diagnostics Inc., Coralville, IA (US)

( * ) Notice: Subject to any disclaimer, the term of this patent is extended or adjusted under 35 U.S.C. 154(b) by 532 days.

(21) Appl. No.: 17/202,191

(22) Filed: Mar. 15, 2021

(65) Prior Publication Data

US 2021/0290055 A1    Sep. 23, 2021

Related U.S. Application Data

(60) Provisional application No. 62/992,037, filed on Mar. 19, 2020.

(51) Int. Cl.
*A61B 3/14* (2006.01)
*A61B 3/00* (2006.01)
(Continued)

(52) U.S. Cl.
CPC .............. *A61B 3/14* (2013.01); *A61B 3/0008* (2013.01); *A61B 3/0025* (2013.01); *A61B 3/12* (2013.01)

(58) Field of Classification Search
CPC ....... A61B 3/14; A61B 3/0008; A61B 3/0025; A61B 3/12
(Continued)

(56) References Cited

U.S. PATENT DOCUMENTS 6,789,900 B2 * 9/2004 Van de Velde ..... A61F 9/00821
351/221
2007/0076169 A1 4/2007 Carnevale
(Continued)

FOREIGN PATENT DOCUMENTS

WO    WO 2017/111580 A1    6/2017
WO    WO 2019/030375 A2    2/2019

OTHER PUBLICATIONS

PCT International Search Report and Written Opinion, PCT Application No. PCT/US2021/022424, dated Jun. 3, 2021, 12 pages.
(Continued)

*Primary Examiner* — Mahidere S Sahle
(74) *Attorney, Agent, or Firm* — Fenwick & West LLP

(57) ABSTRACT

Systems and methods are disclosed herein for adjusting flash intensity based on retinal pigmentation. In an embodiment, a processor determines a retinal pigmentation of a retina of an eye positioned at an imaging device. The processor commands the imaging device to adjust an intensity of a flash component from a first intensity to a second intensity based on the retinal pigmentation. The processor commands the imaging device to capture an image that is lit by the flash component at the second intensity, and receives the image from the imaging device.

18 Claims, 7 Drawing Sheets

(51) Int. Cl.
*A61B 3/10* (2006.01)
*A61B 3/12* (2006.01)

(58) Field of Classification Search
USPC .................................................. 351/206, 221
See application file for complete search history.

(56) References Cited

U.S. PATENT DOCUMENTS

| | | |
|---|---|---|
| 2008/0298756 A1 | 12/2008 | Truitt et al. |
| 2014/0267668 A1 | 9/2014 | Ignatovich et al. |
| 2016/0073877 A1 | 3/2016 | Su et al. |
| 2016/0242734 A1 | 8/2016 | Su et al. |
| 2019/0110753 A1 | 4/2019 | Zhang et al. |

OTHER PUBLICATIONS

European Patent Office, Extended European Search Report and Written Opinion, European Patent Application No. 21770527.6, Mar. 12, 2024, 9 pages.

\* cited by examiner

DYNAMIC ADJUSTMENT OF FLASH INTENSITY BASED ON RETINAL PIGMENTATION

CROSS-REFERENCE TO RELATED APPLICATIONS

This application claims the benefit of U.S. Provisional Patent Application Ser. No. 62/992,037, "Dynamic Adjustment of Flash Intensity Based on Retinal Pigmentation," filed Mar. 19, 2020, the disclosure of which is hereby incorporated by reference herein in its entirety.

BACKGROUND

This invention relates generally to autonomous diagnosis of retinal abnormalities, and more specifically to adjusting a flash intensity of an imaging device based on retinal pigmentation.

Autonomous systems for diagnosing retinal abnormalities capture images of a patient's retina (interchangeably used with the word fundus herein) and analyze those images for abnormalities. The images are captured using pre-set flash intensities. However, like external skin, a fundus of a user may be pigmented, and pigmentation may cause an image to be under-exposed or over-exposed using the pre-set flash intensity. Under-exposure or over-exposure may cause the image to be suboptimal, where biomarkers used to diagnose an abnormality may be obscured, thus preventing a system from diagnosing an abnormality that would have appeared on the image if the image were properly exposed.

Under-exposed or over-exposed images may also be insufficient for diagnosis, thus requiring a patient to sit through multiple images, each image requiring another use of a flash. Repeated exposure to flash by an imaging device may cause damage to a patient's eye, and thus, preventing or reducing the probability that an image is under-exposed or over-exposed will improve patient health, in that fewer flashes will be required to capture a sufficient image of the patient's eye.

SUMMARY

Systems and methods are provided herein for determining a patient's retinal pigmentation, and causing an adjustment to a flash intensity based on the determined pigmentation. For example, retinal pigmentation may be determined based on an initial image being over-exposed or under-exposed, and a flash intensity used to capture a subsequent image may be adjusted based on that over-exposure or under-exposure. As another example, infrared light may be used to determine retinal pigmentation, thus preventing a need for an initial image to be captured from the patient using a flash. As yet another example, an image may be captured of the patient's skin or hair, from which pigmentation may be determined. The systems and methods disclosed herein advantageously prevent over-exposure and under-exposure of captured images once pigmentation is learned, and will prevent the need to unnecessarily expose a patient's eyes to multiple flashes due to unsuccessful imaging.

To these ends and others, in an embodiment, a processor (e.g., of a server) determines a retinal pigmentation of a retina of an eye positioned at an imaging device (e.g., a camera remote from the server). The processor commands the imaging device to adjust an intensity of a flash component from a first intensity to a second intensity based on the retinal pigmentation. The processor then commands the imaging device to capture an image that is illuminated by the flash component at the second intensity, and receives the image from the imaging device. The image may be used to diagnose whether a retinal abnormality is observed in the patient's retina.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION (a) Environment Overview

Figure 1:
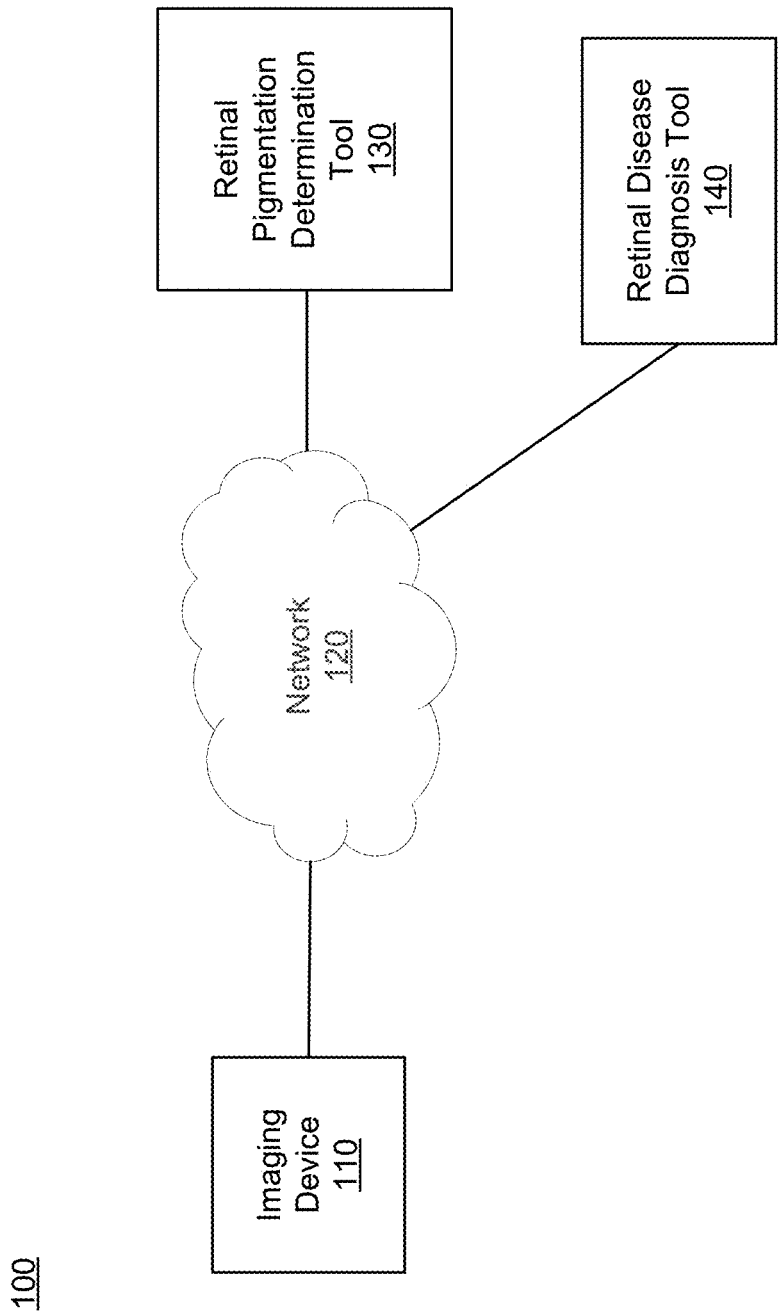
FIG. 1 is an exemplary block diagram of system components in an environment for utilizing a retinal pigmentation determination tool, in accordance with one embodiment.

FIG. 1 is an exemplary block diagram of system components in an environment for utilizing a retinal pigmentation determination tool, in accordance with one embodiment. Environment 100 includes imaging device 110, network 120, retinal pigmentation determination tool 130, and retinal disease diagnosis tool 140. Imaging device 110 is a device configured to capture one or more images of a retina of a patient's eye. Imaging device 110 may be caused to capture such images through manual operation, autonomously as instructed by computer program instructions or external signals (e.g., received from retinal pigmentation determination tool 130), or a combination thereof. Examples of what these images may look like, and how they are derived, are described in commonly-owned U.S. patent application Ser. No. 15/466,636, filed Mar. 22, 2017, the disclosure of which is hereby incorporated by reference herein in its entirety.

After capturing an image, imaging device 110 transmits the image to retinal pigmentation determination tool 130 for processing. While not depicted, in an embodiment, retinal pigmentation determination tool 130 is installed as a module on imaging device 110, and thus the transmission is internal to imaging device 110. In the depicted embodiment, retinal pigmentation determination tool 130 is instantiated on a server remote from imaging device 110, and the image is transmitted over network 120. Network 120 may be any communications network, such as a local area network, a wide area network, the Internet, and the like.

Though not depicted in FIG. 1, one or more additional imaging devices may be used to capture an external image including some or all of a patient (e.g., the patient's skin or hair). The pigmentation of the retina may be determined therefrom.

Retinal pigmentation determination tool 130 receives the image and determines whether the image is suitable for processing. In an embodiment, suitability for processing means that the image is exposed with a designated intensity of light, or within a range of designations of intensity of light, such that biomarkers within the patient's retina can be detected by retinal disease diagnosis tool 140. In another embodiment, suitability for processing means that certain landmarks within the patient's retina are identifiable within the image. Further discussion of how to determine whether an image is suitable for processing is discussed with reference to FIGS. 2-7 below.

A factor that contributes to an image being unsuitable for processing is retinal pigmentation; if a patient's retina is pigmented (either with light or dark pigmentation), the retinal image may be over-exposed or under-exposed if a consistent flash intensity is used when capturing the image. Retinal pigmentation determination tool determines retinal pigmentation and/or necessary adjustments to flash intensity based on retinal pigmentation, and instructs imaging device 110 (or a human operator thereof) to adjust the flash intensity prior to capturing an image, or a further image. Manners in which retinal pigmentation determination tool 130 performs determinations and instructs adjustments is described in further detail with respect to FIG. 3 below.

Retinal disease diagnosis tool 140 autonomously analyzes retinal images and determines, using machine learning analysis of biomarkers therein, a diagnosis. The diagnosis may specifically be a determination that the user has a particular disease, such as diabetic retinopathy, or may be a determination that the user likely has a disease and should thus see a doctor for confirmation and treatment. The manners in which retinal disease diagnosis tool 140 performs the analysis and determines a diagnosis are further discussed in commonly-owned U.S. Pat. No. 10,115,194, the disclosure of which is hereby incorporated by reference herein in its entirety. While depicted as a separate entity from retinal pigmentation determination tool 130, retinal disease diagnosis tool 140 may be instantiated on a same server or set of servers as retinal pigmentation determination tool 130, and may be, in part or in full, installed as a module on imaging device 110, similar to the manner in which retinal pigmentation determination tool 130 may be installed as a module in imaging device 110.

(b) Exemplary Imaging Device Components

Figure 2:
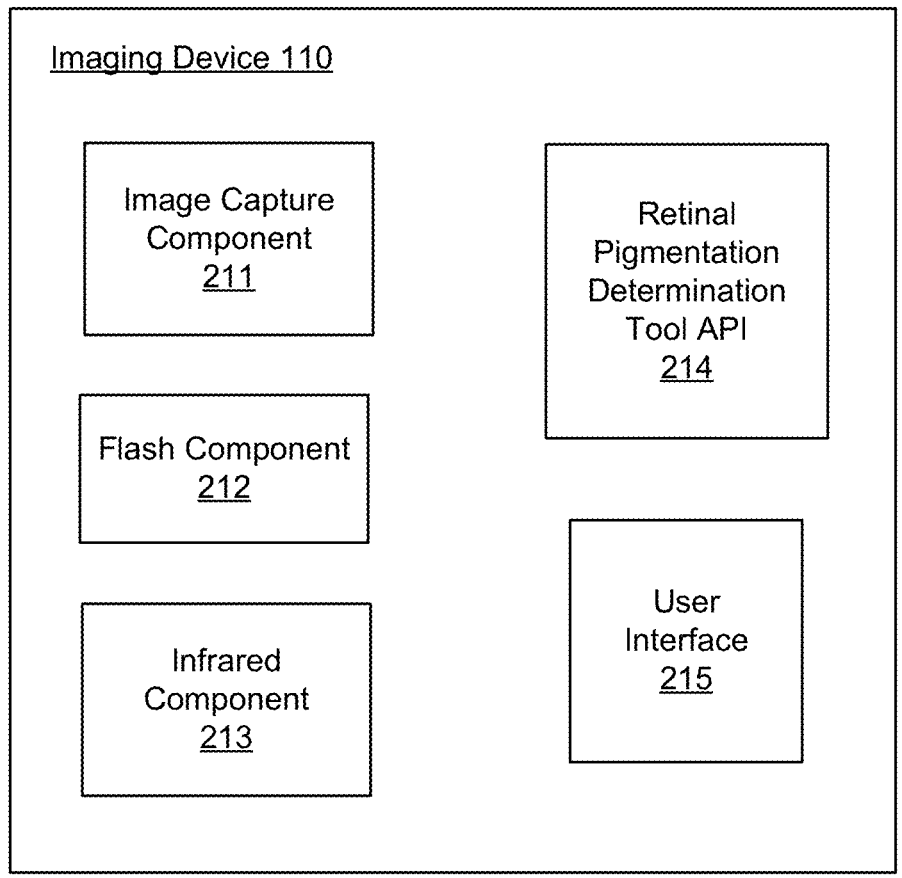
FIG. 2 is an exemplary block diagram of modules and components of an imaging device, in accordance with one embodiment.

FIG. 2 is an exemplary block diagram of modules and components of an imaging device, in accordance with one embodiment. Imaging device 110 includes image capture component 211, flash component 212, infrared component 213, retinal pigmentation determination tool application protocol interface (API) 214, and user interface 215. While not depicted, imaging device 110 may include other components, such as on-board instantiations of either or both of retinal pigmentation determination tool 130 and retinal disease diagnosis tool 140, and any components thereof. Imaging device 110 may include any databases or memory for performing any functions described herein. Imaging device 110 may exclude some depicted components as well. For example, imaging device may exclude infrared component 213.

Image capture component 211 may be any sensor configured to capture an image of a patient's retina. For example, a specialized lens may be used to capture the image of the patient's retina. Flash component 212 may be any component capable of illuminating a patient's retina during the image capture by image capture component 211, and may be configured to emit light in concert with an image capture operation of image capture component 211. Image capture component 211 may also be configured with an external image capture component 211 for capturing an image including a patient's skin and/or hair.

Infrared component 213 is an infrared sensor that is configured to transmit infrared radiation to a patient's retina and determine absorption thereof. Infrared component 213 may generate a heat map showing absorption of the infrared transmission across the patient's retina. Infrared component 213 transmits the absorption determination and/or heat map to a processor (e.g., of retinal pigmentation determination tool 130) for processing with respect to determination of retinal pigmentation of the patient.

Retinal pigmentation determination tool API 214 interfaces with retinal pigmentation determination tool 130 to translate commands from retinal pigmentation determination tool 130 to imaging device 110. Exemplary commands may include a command to capture an image, a command to adjust an intensity of light emitted by flash component 212, and the like. These commands and how they are generated are discussed in further detail with reference to FIG. 3 below.

User interface 215 is an interface with which an operator of imaging device 110 may command imaging device 110 to perform any function it is capable of performing, such as capturing images, adjusting flash intensity, capturing infrared information, and the like. User interface 215 may be any hardware or software interface, and may include physical components (e.g., buttons) and/or graphical components (e.g., on a display, such as a touch screen display). User interface 215 may be located on imaging device 110, may be a device peripheral to imaging device 110, or may be located on a device separated from imaging device 110 by network 120, thus enabling remote operation of imaging device 110.

(c) Exemplary Retinal Pigmentation Determination Tool Components

Figure 3:
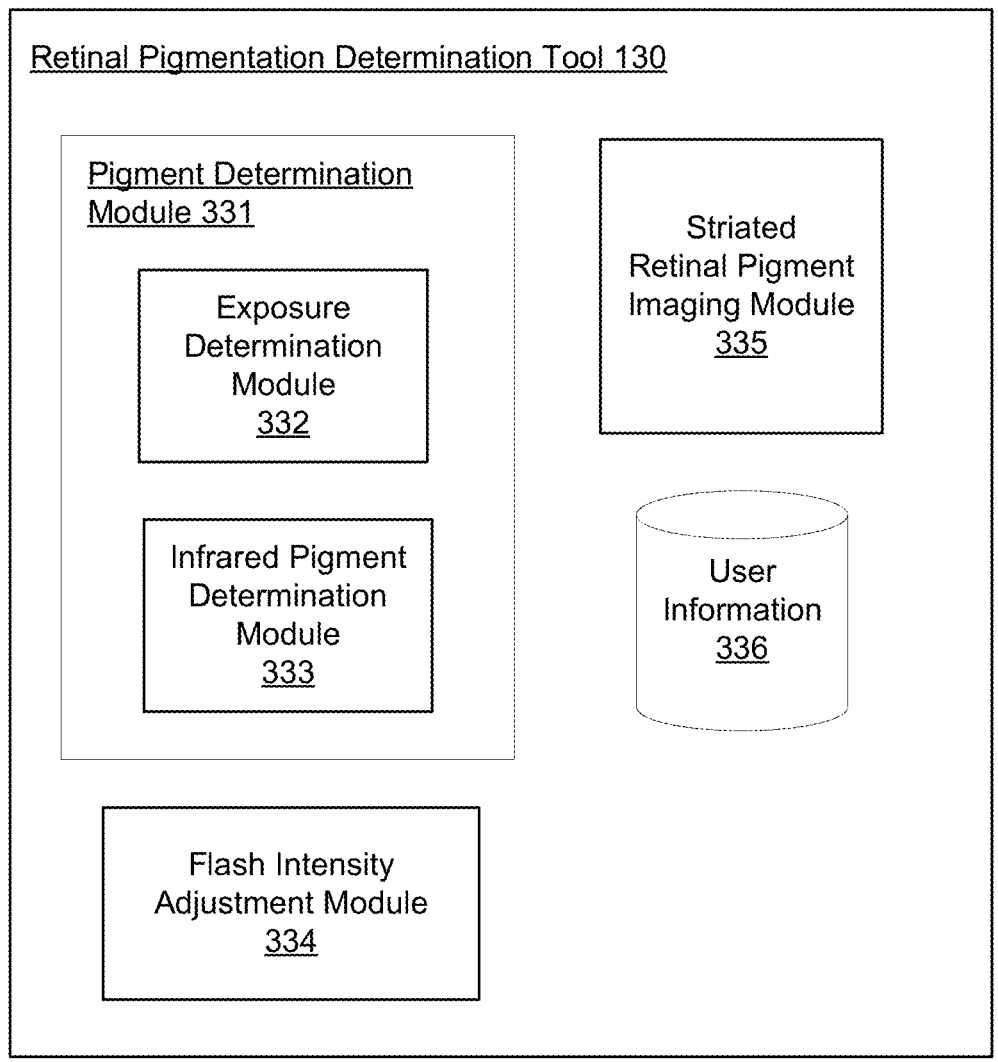
FIG. 3 is an exemplary block diagram of modules and components of a retinal pigmentation determination tool, in accordance with one embodiment.

FIG. 3 is an exemplary block diagram of modules and components of a retinal pigmentation determination tool, in accordance with one embodiment. Retinal pigmentation determination tool 130 includes pigment determination module 331, flash intensity adjustment module 334, and striated retinal pigment imaging module 335. While not depicted, retinal pigmentation determination tool 110 may include other components such as additional modules, and any databases or memory for performing any functions described herein. Retinal pigmentation determination tool 130 may exclude some depicted components as well. For example, retinal pigmentation determination tool 130 may exclude striated retinal pigment imaging module 355.

Pigment determination module 331 determines retinal pigmentation of a patient based on information received from imaging device 110. The information may include an image or a series of images of the retina of the patient, infrared absorption information, and/or a combination thereof. Pigment determination module 331 may execute sub-modules, such as exposure determination module 332 and/or infrared pigment determination module 333. Alternatively, exposure determination module 332 and/or infrared pigment determination module 333 may be stand-alone modules, rather than sub-modules of pigment determination module 331.

Reference is now made to an embodiment where retinal pigmentation is determined based on a retinal image of a patient received from imaging device 110. Exposure determination module 332 determines whether the image is under-exposed, or over-exposed. As used herein, the term under-exposed may refer to the image being captured while the retina of the patient is exposed to insufficient light intensity from flash component 212, thus reducing the odds a biomarker that would appear in a properly exposed image is detected in the under-exposed image due to insufficient illumination. Similarly, the term over-exposed may refer to the image being captured while the retina of the patient is exposed to too much light intensity from flash component 212, thus reducing the odds a biomarker that would appear in a properly exposed image is detected in the over-exposed image due to the overabundance of illumination. The term biomarker, as used herein, is an object in the image that is a part of the patient's retina that corresponds to retinal disease.

Exposure determination module 332 may determine that an image, in part or in full, is over-exposed or under-exposed by analyzing aspects of the captured image (or portions thereof), and determining therefrom a level of exposure. For example, a level of brightness, a level of grayscale (e.g., at individual points, or on average), a level of intensity of color, or any other measure of brightness, intensity, coloration, and the like may be determined. The level of exposure may be determined on a pixel-by-pixel basis, where exposure determination module 332 generates a heat map, each portion of the heat map reflecting the level of exposure of the corresponding pixel in the captured image. Exposure determination module 332 may determine the level of exposure on an aggregate basis for the image. The level of exposure for an image in its entirety may be taken by performing a statistical operation (e.g., mean, median, mode) of the levels of exposure on a pixel-by-pixel basis, or on a group-of-pixels-by-group-of-pixels basis to identify a level of exposure that reflects the image as a whole.

Exposure determination module 332 may determine whether the level of exposure, either for each pixel, for each group of pixels, or for the image as a whole, is within a predefined range of exposure. For example, an over-exposure range, an under-exposure range, and a proper exposure range may be predefined by an administrator of retinal pigmentation determination tool 130. Exposure determination module 332 may determine which of the ranges the level of exposure fits, and may determine, based on the range, whether the image is over-exposed, under-exposed, or properly exposed. Exposure determination module 332 may perform this determination of over-exposure, under-exposure, or proper exposure on the image as a whole, or on different parts of the image based on a group of pixels' level of exposure.

Exposure determination module 332 may determine the level of exposure, either for a pixel, a group of pixels, or a pixel as a whole, using additional information. For example, exposure determination module 332 may compute a similarity of the image (or pixels or groups of pixels thereof) with reference to a reference image with a typical exposure level. A database indicating similarity levels as mapped to levels of exposure may be referenced, and the level of exposure may be determined therefrom. As another example, exposure determination module 332 may filter the image to determine gradient differences in color spaces (e.g., red-green-blue, cyan-magenta-yellow-key, etc.) with respect to image brightness. The gradient differences may be compared to entries of a database that map gradient differences to levels of exposure.

Exposure determination module 332 may determine a pigmentation of the retina based on the level of exposure. In order to determine the pigmentation, exposure determination module 332 may access a data structure that maps a level of exposure to a pigmentation. Any aforementioned level of exposure—that is, the level of exposure as computed on a per-pixel basis, for a group of pixels, the image as a whole—may be mapped to a pigmentation. A map that indicates the pigmentation may be generated on a pixel-by-pixel basis based on each pixel's level of exposure.

Exposure determination module 332 may determine an adjustment value based on the pigmentation and the flash intensity used to capture the image. For example, a data structure may be referenced that indicates, for each type of possible pigmentation, a level of exposure corresponding to each flash intensity. The data structure indicates an adjustment value for that level of exposure. Alternatively, exposure determination module 332 may compute an adjustment value based on the level of exposure, without reference to the pigmentation. In order to perform this adjustment when considering the level of exposure of the image as a whole, exposure determination module 332 may determine a difference between the level of exposure and a predefined proper exposure value, and may assign that difference to be the adjustment value.

In an embodiment, exposure determination module 332 may compute an adjustment value based on the level of exposure for each pixel in the image, or based on the level of exposure for different groups of pixels in the image (e.g., each quadrant of the image may have a different level of exposure calculated). Exposure determination module 332 may compute an adjustment value by maximizing the amount of pixels, or the amount of groups of pixels, that would have a level of exposure after the adjustment that falls within a properly exposed range. For example, if three of four quadrants are over-exposed, and an adjustment value is calculated that, if applied to the levels of exposure of all four quadrants, would cause three of the four quadrants to be properly exposed, and there is no adjustment value that would cause all four quadrants to be properly exposed, then the adjustment value would be applied to maximize the amount of the image that is properly exposed.

In an embodiment, exposure determination module 332 may discount the levels of exposure of pixels, or groups of pixels, that are properly exposed when determining the adjustment value. This is because the properly exposed pixels may be stitched into an image where the improperly exposed images are corrected by way of a flash intensity adjustment, or otherwise considered by analyzing two separate images, when using the images for an intended purpose (e.g., detecting biomarkers). Thus, exposure determination module 332 may determine a level of intensity for an image for use in calculating an adjustment value by considering pixels or groups of pixels that are over- or under-exposed, while ignoring the levels of intensity of properly exposed portions of the images.

Exposure determination module 332 may store, to user information database 336, the adjustment value and/or the adjusted value after the adjustment value is applied. As will be described in further detail below, flash intensity adjustment module 334 may instruct imaging device 110 to adjust its flash intensity based on the adjustment value. During future imaging sessions, retinal pigmentation determination tool 130 may identify the patient and retrieve the flash intensity adjustment value from user information 336 to determine a flash adjustment prior to an image being taken, thus eliminating the need to expose the patient to a flash that would yield an improperly exposed image. Adjustment values may be assigned to each eye of a patient (where images are labeled with which eye (left or right) the image corresponds to), and may be used depending on which eye is being imaged.

In an embodiment, exposure determination module 332 may determine retinal pigmentation and/or exposure values by inputting an image into a machine learning model, and receiving, as output from the machine learning model, the retinal pigmentation. The machine learning model may be trained using images that are labeled as having certain retinal pigmentation and/or exposure values.

Reference is now made to an embodiment where retinal pigmentation is determined based on infrared absorption information of an eye of a patient, as received from imaging device 110. Infrared pigment determination module 333 receives the absorption information and/or heat map from imaging device 110, and computes therefrom the retinal pigmentation of the patient. In an embodiment, infrared pigmentation determination module 333 computes the pigmentation by comparing the absorption information to information in a data structure that maps absorption to pigmentation. In another embodiment, infrared pigmentation determination module 333 inputs the absorption information into a machine learning model, and receives as output from the machine learning model the pigmentation. Other input may also be made into the machine learning model with the absorption information, such as any patient vital, biographical, or demographic information as retrieved from user information database 336 or received with the absorption information from imaging device 110. After determining the pigmentation, pigment determination module 331 may determine an adjustment value using the techniques described above with reference to the exposure determination module 332.

The adjustment value may be additionally informed using other parameters. For example, the flash intensity and/or gain may be compared, in isolation or in combination with other factors (e.g., the gamma setting of imaging device 110), to a statistical parameter (e.g., mean, median, etc.) of the infrared level. Pigment determination module 331 may reference a database with the result of the comparison to determine its corresponding pigmentation, as is mapped to the result of the comparison in the database.

In an embodiment, exposure determination module 332 may determine retinal pigmentation and/or exposure values by inputting an infrared image (or heat map, as described above) into a machine learning model, and receiving, as output from the machine learning model, the retinal pigmentation (or information which can be used to determine the retinal pigmentation. The machine learning model may be a trained image level classifier that outputs flash exposure time and intensity from the infrared image. The classifier may use predefined features extracted from the infrared image to output the flash exposure time and intensity. Flash exposure time and intensity may be used to determine, either by referencing a database, or by inputting the flash exposure time and intensity into a trained classifier that is trained to translate flash exposure time and intensity into pigmentation, a pigmentation of the retina. The resultant exposure time and intensity received from the model may be derived from representative normative database for various pigmentations.

Flash intensity adjustment module 334 transmits a command to imaging device 110 to have the flash intensity emitted by flash component 212 adjusted. The command may include an amount by which to adjust the flash intensity, or may include a new flash intensity value. In an embodiment, adjustments to the flash intensity described above as performed by pigment determination module 331 and/or its sub-modules may instead be performed by flash intensity adjustment module 334.

In an embodiment, retinal pigmentation determination tool 130 may categorize a retina into a set of known retina types or pigmentations, where each known type or pigmentation of the set has a corresponding exposure time and/or flash intensity mapped to it in an electronic data structure. For example, retinal pigmentation determination tool 130 may perform a statistical operation on an entire infrared image (e.g., or an infrared heat map), or on a specific feature of an infrared image (e.g., pixel or group of pixels, or feature such as optic disc, fovea, or blood vessels), and may determine a mapping of the statistical operation to a known retina type. Retinal pigmentation determination tool 130 may determine retinal pigmentation therefrom. As another example, retinal pigmentation determination tool 130 may use an encoder in combination with a clustering algorithm (e.g., k-means clustering), and may map the output of the encoder to a matching one of the known retinal types or pigmentations. As another example, retinal pigmentation tool 130 may input a retinal image into a classification neural network and receive, as output, the known retinal type. As yet another example, one or more images of an iris may be used, in isolation, or in addition, to the above-mentioned examples, as an input to determine a known retina type. Retinal pigmentation determination tool 130 may determine an exposure time and/or a flash intensity to capture an image of the retina based on the mapping in the electronic data structure. The electronic data structure may be continuously refined, e.g., by storing a critical metric or embedding of an infrared image and the resulting image quality score of a fundus color image and feeding that into a classifier data as updated training data.

Striated retinal pigment imaging module 335 identifies striations in retinal pigmentation, and determines remedial measures to ensure that a retinal image that is properly exposed can be obtained or constructed. Striated retinal pigment imaging module 335 may use levels of exposure, a pixel-by-pixel or group-of-pixel exposure map, infrared absorption information, or any other information as described above to determine whether a retinal image indicates that a patient has striated pigmentation in the patient's retina.

In an embodiment, striated pigment imaging module 335 may determine that groups of consecutive pixels that exceed a predetermined amount of pixels in the group have a level of intensity or a level of exposure (e.g., as received using infrared or intensity information) that differs from a neighboring group of pixels by a predetermined amount. For example, groups of pixels with high levels of intensity that are adjacent to groups of pixels with low levels of intensity may indicate different pigmentation at the points in the patient's retina to which those pixels correspond. Striated retinal pigment imaging module 335 may determine therefrom that the retina of the patient is striated. In order to prevent or minimize false positives, striated retinal pigment imaging module 335 may consider groups of pixels that are at least a threshold size (e.g., at least thirty pixels wide), to ensure that it is pigmentation that is causing a change in level of intensity or exposure, rather than a biomarker or other artifact. While a common circumstance is stripes—or striations—that are vertical or horizontal across the retina with different pigmentation, wherever the term striation is used herein, non-striped patterns of differing pigmentation are within the scope of the disclosure. For example, tessellations may be identified wherever the term striation is used herein. Tessellations may be detected using gradients in an image, edge detectors, oriented edge detectors, bag of words, dictionary learning based on a histogram of patches, template matching, and the like.

Striated pigment imaging module 335 may alternatively, or additionally, determine that the retina is striated using computer vision. In an embodiment, striated pigment imaging module 335 may determine whether edges are present (e.g., a boundary between two pigmentations) using computer vision. Striated pigment imaging module may, where edges are present, determine striation using static or adaptive thresholding techniques, such as determining whether the difference in pigmentation on each side of an edge is different by a threshold amount (e.g., threshold intensity or infrared information). Striated pigment imaging module 335 may, in a computer vision model, perform Hough transforms at one or more angles to identify semi-linear objects, which may represent edges. Striated pigment imaging module 335 may, additionally or alternatively, compare contours on various color channels to identify striations, the contour comparison aiding in striation detection where a color channel is part of the pigmentation in which striations are less visible than is typical. Statistical analysis may be performed on infrared and intensity distributions, where standard deviations are applied to confirm the likelihood that a striation has been detected. Furthermore, neural networks, such as a classification neural network and a segmentation neural network, may be trained and used to identify striations.

Striated retinal pigment imaging module 335 may command imaging device 110 to capture two or more retinal images, each at differing flash intensities, to cause different exposure levels corresponding to the level of intensity required to properly expose at the two or more intensities corresponding to the striations. Striated retinal pigment imaging module 335 may then stitch together the two or more images, using portions that are properly exposed from each image to create an aggregate image that is properly exposed throughout. Alternatively, striated retinal pigment imaging module 335 may maintain each image separately for further analysis. For example, a module that performs a diagnosis of retinal disease may analyze the properly exposed portions of each image to detect biomarkers, and may output the diagnosis based on biomarkers identified across the two or more images.

User information database 336 is a database that may maintain a profile for each patient. The profile may include any collected information, including biographic information (e.g., name, height, weight), demographic information (e.g., ethnicity, geographic location), and any other information (e.g., health records).

Though not depicted, in an embodiment an image including a patient's hair and/or skin is received by retinal pigmentation determination tool 130. Retinal pigmentation tool may determine therefrom the retinal pigmentation of the patient. As an example, retinal pigmentation tool 130 may reference a data structure that corresponds a patient's hair and/or skin color to a retinal pigmentation, and takes the mapped retinal pigmentation value as an assumed retinal pigmentation of the patient. As another example, retinal pigmentation tool 130 may input the image or data derived therefrom into a machine learning model that is trained to output a retinal pigmentation. This may be performed before an image is captured of the retina of the patient, and may be used to adjust the flash intensity prior to capturing the image in any manner described herein.

(d) Exemplary Computing Machine Architecture

Figure 4:
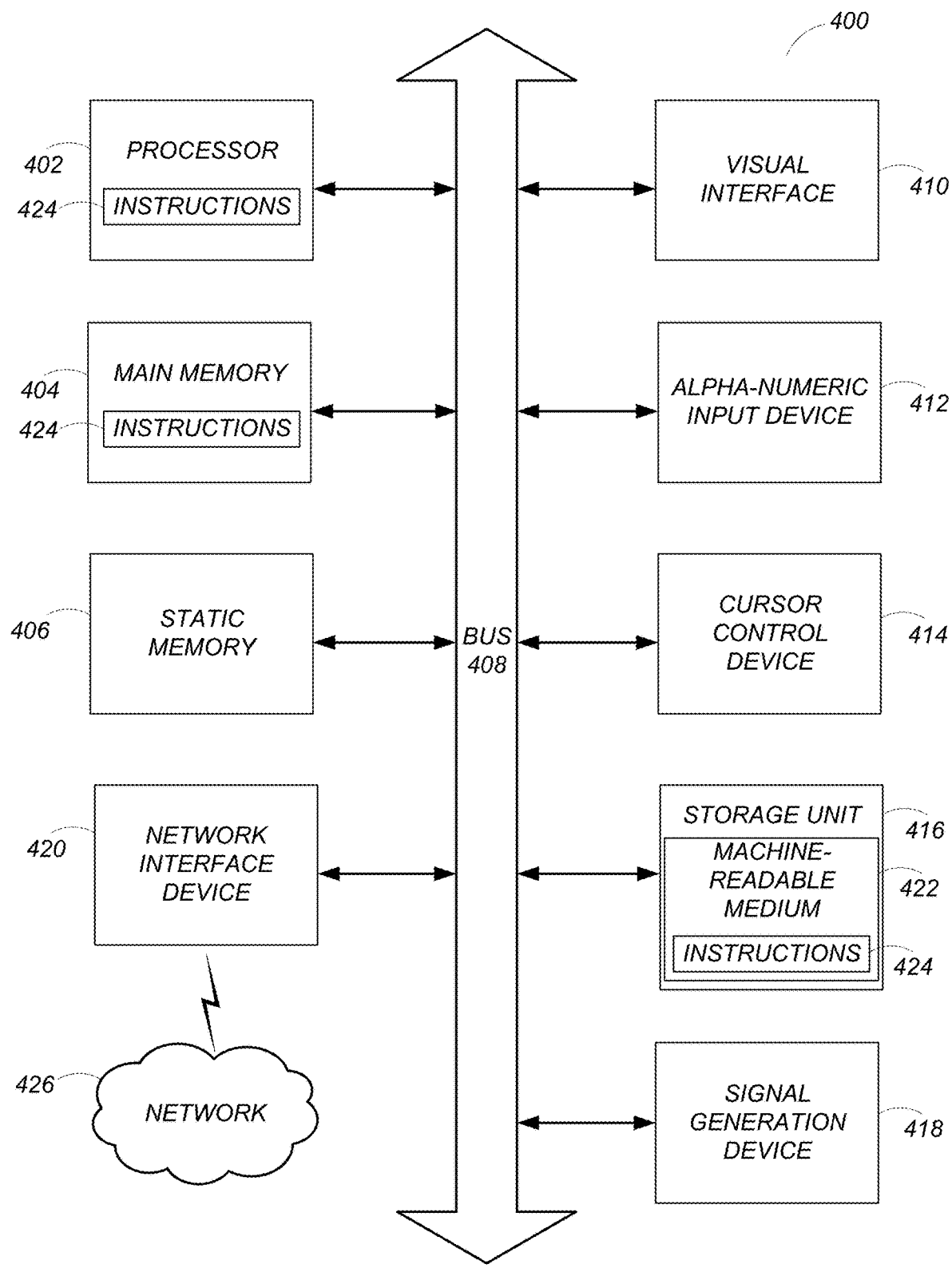
FIG. 4 is a block diagram illustrating components of an example machine able to read instructions from a machine-readable medium and execute them in a processor (or controller).

FIG. 4 is a block diagram illustrating components of an example machine able to read instructions from a machine-readable medium and execute them in a processor (or controller). Specifically, FIG. 4 shows a diagrammatic representation of a machine in the example form of a computer system 400 within which program code (e.g., software) for causing the machine to perform any one or more of the methodologies discussed herein may be executed. The program code may be comprised of instructions 424 executable by one or more processors 402. In alternative embodiments, the machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a personal digital assistant (PDA), a cellular telephone, a smartphone, a web appliance, a network router, switch or bridge, or any machine capable of executing instructions 424 (sequential or otherwise) that specify actions to be taken by that machine. Further, while only a single machine is illustrated, the term "machine" shall also be taken to include any collection of machines that individually or jointly execute instructions 124 to perform any one or more of the methodologies discussed herein.

The example computer system 400 includes a processor 402 (e.g., a central processing unit (CPU), a graphics processing unit (GPU), a digital signal processor (DSP), one or more application specific integrated circuits (ASICs), one or more radio-frequency integrated circuits (RFICs), or any combination of these), a main memory 404, and a static memory 406, which are configured to communicate with each other via a bus 408. The computer system 400 may further include visual display interface 410. The visual interface may include a software driver that enables displaying user interfaces on a screen (or display). The visual interface may display user interfaces directly (e.g., on the screen) or indirectly on a surface, window, or the like (e.g., via a visual projection unit). For ease of discussion the visual interface may be described as a screen. The visual interface 410 may include or may interface with a touch enabled screen. The computer system 400 may also include alphanumeric input device 412 (e.g., a keyboard or touch screen keyboard), a cursor control device 414 (e.g., a mouse, a trackball, a joystick, a motion sensor, or other pointing instrument), a storage unit 416, a signal generation device 418 (e.g., a speaker), and a network interface device 420, which also are configured to communicate via the bus 408.

The storage unit 416 includes a machine-readable medium 422 on which is stored instructions 424 (e.g., software) embodying any one or more of the methodologies or functions described herein. The instructions 424 (e.g., software) may also reside, completely or at least partially, within the main memory 404 or within the processor 402 (e.g., within a processor's cache memory) during execution thereof by the computer system 400, the main memory 404 and the processor 402 also constituting machine-readable media. The instructions 424 (e.g., software) may be transmitted or received over a network 426 via the network interface device 420.

While machine-readable medium 422 is shown in an example embodiment to be a single medium, the term "machine-readable medium" should be taken to include a single medium or multiple media (e.g., a centralized or distributed database, or associated caches and servers) able to store instructions (e.g., instructions 424). The term "machine-readable medium" shall also be taken to include any medium that is capable of storing instructions (e.g., instructions 424) for execution by the machine and that cause the machine to perform any one or more of the methodologies disclosed herein. The term "machine-readable medium" includes, but not be limited to, data repositories in the form of solid-state memories, optical media, and magnetic media.

(e) Exemplary Image Exposures

Figure 5:
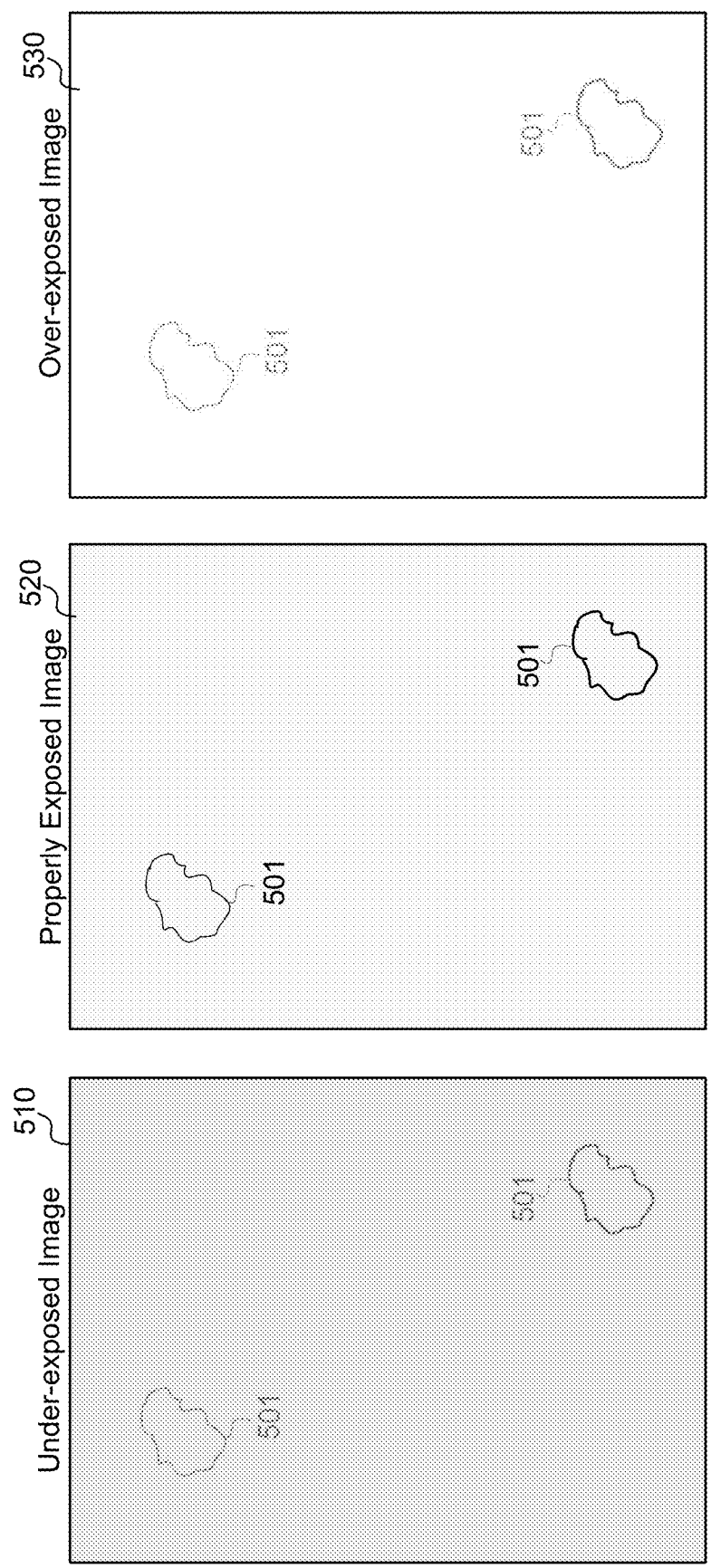
FIG. 5 depicts exemplary images at various levels of exposure, in accordance with one embodiment.

FIG. 5 depicts exemplary images at various levels of exposure, in accordance with one embodiment. Image 510 is an under-exposed image, and includes biomarkers 501. Biomarkers 501 are difficult to make out due to shadowing caused from the underexposure of the image. Image 520 is a properly exposed image, and also includes biomarkers 501, which are easy to make out. Image 530 is an over-exposed image, and also includes biomarkers 501, which are difficult to make out because the over-exposure caused biomarkers to be obscured by an intensity of light that caused biomarkers 501 to have their features appear faint or invisible. A machine learning model or pattern matching tool or component thereof may be unable to detect biomarkers 501 from the over-exposed or under-exposed images because the biomarkers may blend in with the background, whereas the biomarkers of the properly exposed image 520 has features that are easily distinguished from their backgrounds.

Figure 6:
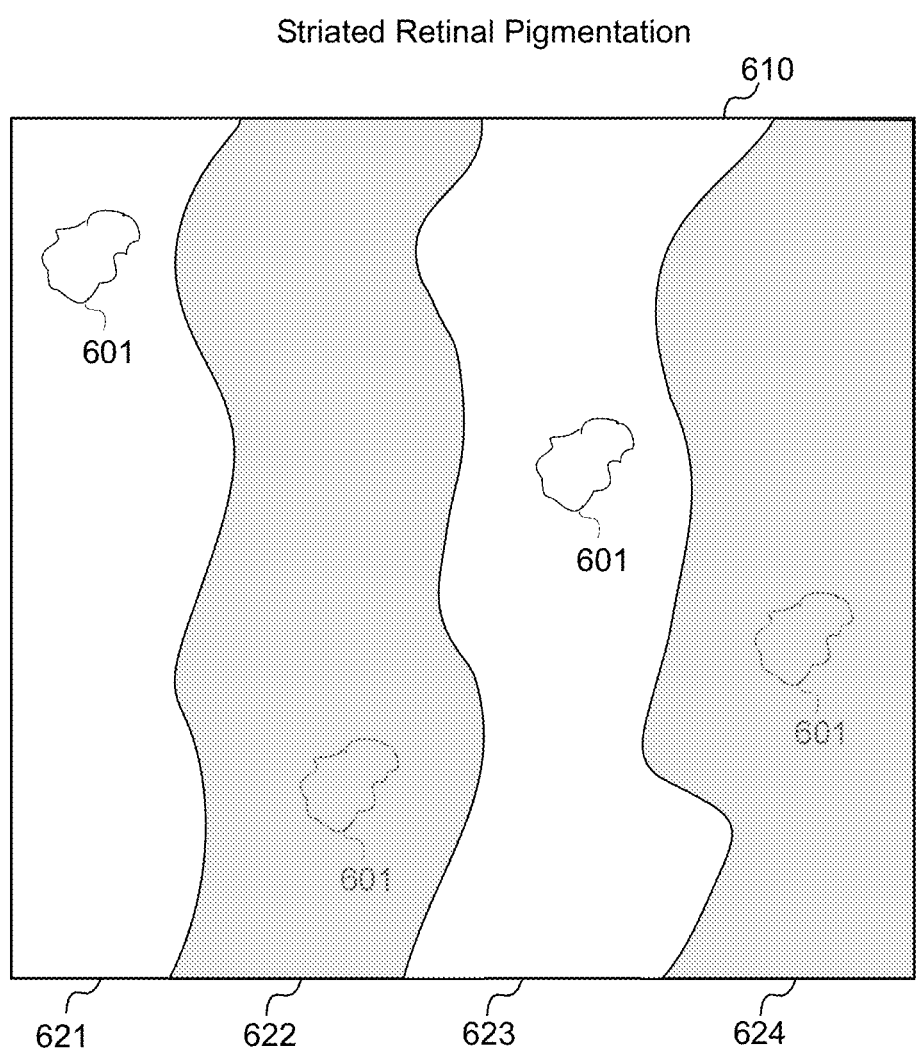
FIG. 6 depicts an exemplary image of a retina having striated retinal pigmentation, in accordance with one embodiment.

FIG. 6 depicts an exemplary image of a retina having striated retinal pigmentation, in accordance with one embodiment. Image 600 includes sections 621, 622, 623, and 624. As depicted, each section is a group of pixels having a shared pigmentation that deviates from each adjacent section thereto. While sections 621 and 623 are depicted as having the same pigmentation relative to one another, as are sections 622 and 624, there may be more than two different types of pigmentations, with some or no commonality in pigmentation at each section. Biomarkers 601 are depicted within each section, though biomarkers 601 may or may not be present in a given section, and more than one biomarker 601 may be present in a given section. As was the case with FIG. 5, biomarkers 601 may be obscured by pigmentation in the image, thus requiring an adjustment to a flash intensity for two or more additional images in order to properly expose each striation.

(f) Exemplary Data Flow for Adjusting Retinal Imaging Flash Intensity

Figure 7:
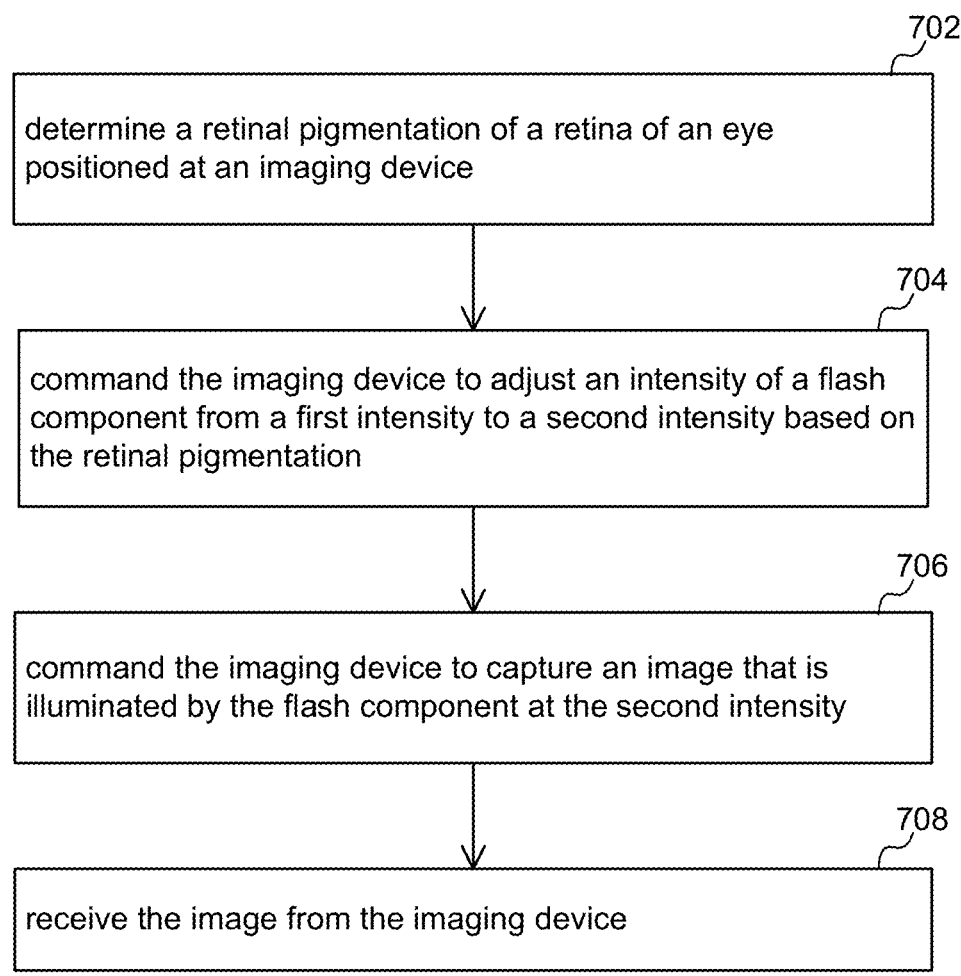
FIG. 7 depicts an exemplary flow chart for adjusting flash intensity based on retinal pigmentation, in accordance with one embodiment.

FIG. 7 depicts an exemplary flow chart for adjusting flash intensity based on retinal pigmentation, in accordance with one embodiment. Process 700 begins with one or more processors (e.g., processor 202) of a device used to run retinal pigmentation determination tool 130 determining 702 a retinal pigmentation of a retina of an eye positioned at imaging device 110. The determining 702 may be performed by pigment determination module 331, which may execute exposure determination module 332 and/or infrared pigment determination module 333 to obtain information necessary to determine the retinal pigmentation. Retinal pigmentation determination tool 130 may then command 704 the imaging device to adjust an intensity of a flash component (e.g., flash component 212) from a first intensity to a second intensity based on the retinal pigmentation. For example, flash intensity adjustment module 334 may command imaging device 110 to adjust the intensity of the flash component from a default intensity to a lower intensity to avoid over-exposure of a light-pigmented retina. The commanding may be performed by transmission of an instruction using an API configured to facilitate communication between imaging device 110 and retinal pigmentation determination tool 130.

Retinal pigmentation determination tool 130 may then command 706 imaging device 110 to capture an image that is illuminated by the flash component at the second intensity, and may receive 708 the image from the imaging device. Further processing may be performed, such as determining whether the image is properly exposed and capturing additional images if the image is wholly, or partially (e.g., in the case of a striated retina) improperly exposed. When all portions of the patient's retina are captured by one or more properly exposed images, retinal pigmentation determination tool 130 may pass the one or more images to another tool, such as a tool that takes the image(s) as input and outputs a diagnosis of retinal disease.

(g) Summary

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method for adjusting flash intensity based on retinal pigmentation, the method comprising:
   determining a retinal pigmentation of a retina of an eye positioned at an imaging device by:
      commanding the imaging device to obtain feedback by flashing an infrared signal at the retina;
      receiving the feedback from the imaging device, the feedback indicative of absorption of the infrared signal by the retina; and
      determining the retinal pigmentation of the eye based on the feedback;
   commanding the imaging device to adjust an intensity of a flash component from a first intensity to a second intensity based on the retinal pigmentation;
   commanding the imaging device to capture an image that is illuminated by the flash component at the second intensity; and
   receiving the image from the imaging device.

2. The method of claim 1, wherein determining the retinal pigmentation of the eye positioned at the imaging device comprises:
   receiving a first image of the eye from the imaging device;
   determining whether the first image is underexposed; and
   responsive to determining that the first image is underexposed, determining the second intensity to be an increased intensity relative to the first intensity.

3. The method of claim 1, wherein determining the retinal pigmentation of the eye positioned at the imaging device comprises:
   receiving a first image of the eye from the imaging device;
   determining whether the first image is overexposed; and
   responsive to determining that the first image is overexposed, determining the second intensity to be a decreased intensity relative to the first intensity.

4. The method of claim 1, wherein commanding the imaging device to adjust the intensity of the flash component comprises transmitting an instruction using an application protocol interface (API).

5. The method of claim 1, wherein the first intensity is at least one of a default intensity or a last-used intensity.

6. The method of claim 1, further comprising:
   determining whether the received image is properly exposed; and
   responsive to determining that the received image is not properly exposed, commanding the imaging device to capture an additional image using a third intensity.

7. The method of claim 1, wherein determining the retinal pigmentation of the retina comprises identifying a plurality of pigmentations within the retina, and wherein the second intensity is determined based on a first retinal pigmentation of the plurality of pigmentations, the method further comprising:
   commanding the imaging device to adjust an intensity of the flash component from the second intensity to a third intensity based on a second retinal pigmentation of the plurality of pigmentations;
   commanding the imaging device to capture an additional image that is lit by the flash component at the third intensity; and
   receiving the additional image from the imaging device.

8. The method of claim 1, further comprising diagnosing a retinal condition of the retina based on features of the image.

9. A computer program product for adjusting flash intensity based on retinal pigmentation, the computer program product comprising a non-transitory computer-readable storage medium containing computer program code for: determining a retinal pigmentation of a retina of an eye positioned at an imaging device by: commanding the imaging device to obtain feedback by flashing an infrared signal at the retina; receiving the feedback from the imaging device, the feedback indicative of absorption of the infrared signal by the retina; and determining the retinal pigmentation of the eye based on the feedback; commanding the imaging device to adjust an intensity of a flash component from a first intensity to a second intensity based on the retinal pigmentation; commanding the imaging device to capture an image that is illuminated by the flash component at the second intensity; and receiving the image from the imaging device.

10. The computer program product of claim 9, wherein the computer program code for determining the retinal pigmentation of the eye positioned at the imaging device comprises computer program code for:
    receiving a first image of the eye from the imaging device;
    determining whether the first image is underexposed; and
    responsive to determining that the first image is underexposed, determining the second intensity to be an increased intensity relative to the first intensity.

11. The computer program product of claim 9, wherein the computer program code for determining the retinal pigmentation of the eye positioned at the imaging device comprises computer program code for:
    receiving a first image of the eye from the imaging device;
    determining whether the first image is overexposed; and
    responsive to determining that the first image is overexposed, determining the second intensity to be a decreased intensity relative to the first intensity.

12. The computer program product of claim 9, wherein the computer program code for commanding the imaging device to adjust the intensity of the flash component comprises computer program code for transmitting an instruction using an application protocol interface (API).

13. The computer program product of claim 9, wherein the first intensity is at least one of a default intensity or a last-used intensity.

14. The computer program product of claim 9, wherein the computer program code further comprises computer program code for:
    determining whether the received image is properly exposed; and
    responsive to determining that the received image is not properly exposed, commanding the imaging device to capture an additional image using a third intensity.

15. The computer program product of claim 9, wherein the computer program code for determining the retinal pigmentation of the retina comprises computer program code for identifying a plurality of pigmentations within the retina, and wherein the second intensity is determined based on a first retinal pigmentation of the plurality of pigmentations, the computer program code further comprising computer program code for:

commanding the imaging device to adjust an intensity of the flash component from the second intensity to a third intensity based on a second retinal pigmentation of the plurality of pigmentations;

commanding the imaging device to capture an additional image that is lit by the flash component at the third intensity; and receiving the additional image from the imaging device.

16. The computer program product of claim 9, wherein the computer program code further comprises computer program code for diagnosing a retinal condition of the retina based on features of the image.

17. A computer program product for adjusting flash intensity based on retinal pigmentation, the computer program product comprising a computer-readable storage medium containing computer program code that comprises: a first module for determining a retinal pigmentation of a retina of an eye positioned at an imaging device by: commanding the imaging device to obtain feedback by flashing an infrared signal at the retina; receiving the feedback from the imaging device, the feedback indicative of absorption of the infrared signal by the retina; and determining the retinal pigmentation of the eye based on the feedback; a second module for commanding the imaging device to adjust an intensity of a flash component from a first intensity to a second intensity based on the retinal pigmentation; a third module for commanding the imaging device to capture an image that is illuminated by the flash component at the second intensity; and a fourth module for receiving the image from the imaging device.

18. The computer program product of claim 17, wherein the first module comprises a sub-module for:

receiving a first image of the eye from the imaging device;

determining whether the first image is underexposed; and responsive to determining that the first image is underexposed, determining the second intensity to be an increased intensity relative to the first intensity.

* * * * *